United States Patent [19]

Barnett

[11] 4,351,938

[45] Sep. 28, 1982

[54] ANTICOAGULANT SUBSTANCE

[75] Inventor: William E. Barnett, Clearwater, Fla.

[73] Assignee: Riker Laboratories, Inc., Northridge, Calif.

[21] Appl. No.: 151,163

[22] Filed: May 19, 1980

[51] Int. Cl.$^3$ .................... C08B 37/10; A61K 31/725
[52] U.S. Cl. ........................................ 536/21; 424/183
[58] Field of Search ........................... 424/183; 536/21

[56] References Cited

U.S. PATENT DOCUMENTS 3,766,167 10/1973 Lasker et al. .................. 260/211 R

OTHER PUBLICATIONS

Rosenberg, *Proc. Natl. Acad. Sci.*, vol. 76, No. 3, pp. 1218–1222, (1979).
Hirano et al., *Connective Tissue Research* vol. 3, pp. 73–79, (1975).
Shively et al., *Biochemistry*, vol. 15, No. 18, pp. 3932–3942, (1976).
Lindahl et al., *Proc. Nat'l Acad. Sci.*, vol. 76, No. 7, pp. 3198–3202, (1979), Biochemistry Section.
Barrowcliffe et al., British Journal of Hematology, vol. 41, pp. 573–583, (1979).
The Merck Index, 7th Edition, p. 511, Merck & Co., Inc. (1960).

*Primary Examiner*—John M. Ford
*Attorney, Agent, or Firm*—Cruzan Alexander; Donald M. Sell; Donald C. Gipple

[57] ABSTRACT

Partially depolymerized heparin products having particular analyzable reducing end groups, a process for their preparation and their use as anticoagulants and antithrombotics.

7 Claims, No Drawings

ANTICOAGULANT SUBSTANCE

This invention relates to partially depolymerized heparin products having particular analyzable reducing end groups, to their use as anticoagulants and antithrombotics and to a process for their preparation.

Heparin is a mucopolysaccharide composed of amino sugar and uronic acid residues. It can be obtained from beef, porcine, sheep, whale or other mammalian tissue by extraction with a solution of potassium acetate, alkaline ammonium sulfate and the like. The commercial product (USP heparin) is available from several sources, generally as an alkali metal or alkaline earth salt (most commonly as sodium heparin).

Heparin is probably the most effective available medication for treating the extension of established venous and arterial thrombi and recently it has been used for preventing thrombosis as well. In both areas of treatment, bleeding or hemorrhaging has been a major problem, some investigators reporting the incidence of hemorrhaging to be as high as 35 percent. Indeed, this is the major limitation of the therapeutic use of heparin, bleeding occurring at a heparin level which is only marginally greater than that which is required to prevent extension of thrombi. Thus, a heparin product having an increased ratio of antithrombotic to hemorrhagic properties would represent an important advance in both therapy and prophylaxis.

Until approximately ten years ago the antithrombotic/hemorrhagic effect of heparin was equated with its anticoagulant effect, i.e. its effect on blood clotting in vitro. Over the last five years, however, it has become clear that different heparin fractions have different anticoagulant effects, that bleeding can be increased by an effect on platelets and that the precise anticoagulant effect responsible for its antithrombotic properties is uncertain. In other words, the ratio between the antithrombitic and hemorrhagic properties of heparins can vary considerably from fraction to fraction.

Heparin is heterogeneous at the molecular level, i.e. it contains polymeric chains of varying lengths and compositions. Thus, a heparin extract of a mammalian tissue would be expected to contain polymer chains ranging in molecular weight from possibly as low as 5,000 to as high as 50,000 daltons and made up of a variety of monosaccharide units, including glucuronic acid, N-acetyl glucosamine, N-sulfated glucosamine, iduronic acid, o-sulfated glucosamine and o-sulfated iduronic acid residues. Furthermore, there are a multitide of possible arrangements of these residues. The following passage and formula from an article by Rosenberg and Rosenberg (appearing in Drug Therapy, September 1979, pages 26-36, at 28) are representative of current information in this area:

During the past few decades, investigators in this field have identified the various types of monosaccharides present within heparin, established the bond configurations that join these elements, and determined the arrangement of these entities with respect to their nearest neighbors. It has been shown, for example, that nonsulfated iduronic acid residues seldom occur and that sulfated iduronic acid moieties are four to five times more frequent than glucuronic acid residues. Furthermore, N-sulfated glucosamine constitutes approximately 90% of the hexosamine residues, with N-acetylated glucosamine making up the remaining small fraction of hexosamine moieties. Nonsulfated, nonacetylated glucosamine residues are rarely observed in heparin preparations.

There have been a number of attempts to correlate the structure of heparin with its anticoagulant properties. Only recently, however, has it been realized that what is commonly referred to as "heparin" comprises a host of mucopolysaccharide species with slightly different primary sequences.

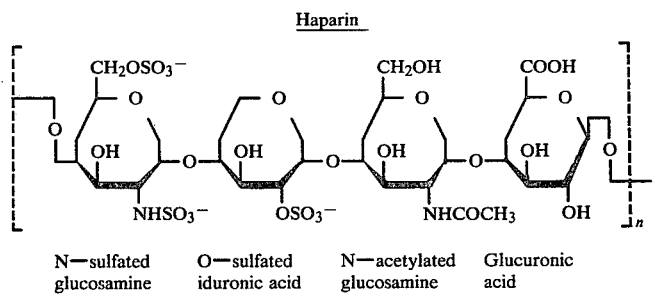

N—sulfated glucosamine    O—sulfated iduronic acid    N—acetylated glucosamine    Glucuronic acid The sequence shown above represents only one of the many possible arrangements of hexosamine and uronic acid residues that exist within the polysaccharide chain of heparin.

Thus, heparin has a considerable degree of polydispersity in molecular size, variations in the ratio of glucuronic acid to induronic acid, alterations in the amount of sulfate ester and N-sulfation, and differing extents of N-acetylation. Changes in any of these parameters have been correlated only to a very limited extent with heparin's antithrombotic potency. Accordingly, it has been widely assumed that its antithrombotic activity is not traceable to a single specific heparin structure, and in any event, no precise relationship between its structure and function is currently known, although significant progress has recently been reported by Rosenberg and Lindahl.

Efforts have been made to increase the ratio of the desired antithrombotic activity to the undesirable hemorrhagic property of heparin by chemical and/or physical modification thereof. Also, low molecular weight modifications have been sought with the hope that they would be orally absorbable and a number of efforts have been made to synthesize chemical compounds and polymers (termed heparinoids) having structures similar to natural heparin and possessed of equivalent or superior properties. Perhaps the most pertinent from the point of view of the present invention is work relating to (1)

physical separation of natural heparins into active and inactive forms and fractions varying in molecular weight and pharmaceutical properties (Rosenberg and Lam. Proc. Natl. Acad. Sci., USA, Vol. 76, No. 3, pages 1218-1222, April 1979); (2) enzymatic depolymerization (U.S. Pat. No. 3,766,167, Laskar et al, utilizing heparinase); (3) chemical depolymerizations (base-catalyzed depolymerization: Hirano et al, Connective Tissue Research, 1975, Vol, 3, pages 73-79, and nitrous acid depolymerization: Shively and Conrad, Biochemistry, Vol. 15, No. 18 (1976), pages 3932-3942 and others cited therein; also Rosenberg and Rosenberg, ibid.).

However, none of the foregoing has resulted in a practical product (and none shows substantial promise for doing so). Thus, the physical fractionation and enzymatic depolymerization of natural heparin, (1) and (2), have been very difficult and have resulted in only very small quantities of product. These could never be made available to the public since the necessary processing would result in, at the very least, a hundred fold increase in cost compared to USP heparin. The chemical depolymerization processes (3) have resulted only in products having very low average molecular weights (e.g. in the range of 1,000 daltons or below) which have no significant antithrombotic activity.

DETAILED DESCRIPTION OF THE INVENTION

The present invention relates to chemically partially depolymerized heparin having
(1) a weight average molecular weight of from about 2,000 to 7,000 daltons, when determined by HPLC (high pressure liquid chromatography, as described hereinafter) using 1.5 molar aqueous sodium chloride as the mobile phase and dextrans as the standard,
(2) a polydispersity (D) of less than about 2.5, and
(3) analyzable reducing end groups of which a majority are anhydromannose groups, i.e.

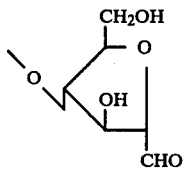

This product is chemically unique and it appears to have an improved ratio of antithrombotic to hemorrhagic activity compared to standard heparin. This is demonstrated in terms of an increased therapeutic index, as will be shown herein. It can be administered in the same way as USP heparin, i.e. ordinarily intravenously or subcutaneously. It is prepared from natural heparin (ordinarily commercial USP heparin or its equivalent is utilized as the starting material) in excellent (i.e. up to quantitative) yields. The preparative process, which comprises the controlled partial depolymerization of heparin with nitrous acid, represents only a minimal additional cost burden compared to USP heparin. It produces directly a product having a surprisingly narrow molecular weight range which requires no further fractionation (i.e. having polydispersity, D, below about 2.5 as noted previously).

Also contemplated is a method for inhibiting the coagulation of blood (i.e. for treating the extension of established venous and arterial thrombi and for preventing the formation of thrombi) which comprises mixing a partially depolymerized heparin as defined above with blood.

The values obtained for the molecular weights of the polymers of the present invention (and of naturally occurring heparin and other chemical and physical variations thereof) vary to some extent with the particular test method used, and it is therefore necessary in referring to test results, ranges of values, etc. to specify the method (and also the test conditions). The high pressure liquid chromatography method described by Petracek and Sugisaka in the Federation Proceedings, Vol. 36, No. 1, January 1977, pages 89-92, has been found to be particularly dependable for determining the molecular weights of the polymers of the present invention and has therefore been adopted herein (frequently being referred to simply as HPLC).

Both 0.5 molar aqueous sodium sulfate and 1.5 molar aqueous sodium chloride have been used as the mobile phase in carrying out the HPLC molecular weight determinations, and other salts and other concentrations could be used as well. Although the absolute values obtained in these two systems differ, there is a definite relationship between them and a measured value in one system can be readily converted into the other. The 1.5 molar sodium chloride system is presently preferred. Although it tends to be very corrosive of equipment with which it comes into contact, the strict exclusion of air and other oxidizing agents from contact therewith has been found to obviate this problem.

Three complementary test values, all based upon HPLC data (and all being well known to those skilled in the art), are utilized. The first, peak retention time molecular weight, is determined quickly and easily as the data is being generated and is conveniently used in monitoring and/or controlling the course of the depolymerization reaction. The others, the weight average molecular weight and number average molecular weight, take longer to calculate but can be used to provide a more meaningful characterization of the polymeric product. Thus, the weight average molecular weight is perhaps the best single value of the molecular weight of a polymer sample and the ratio of the weight average molecular weight to the number average molecular weight, conventionally referred to as polydispersity (D), is a generally recognized measurement of the overall sharpness or breadth of the range of the molecular weights of the polymer chains therein.

The weight average molecular weight of commercial (USP) heparin as determined by the various available analytical methods is reported to lie between about 10,000 and 25,000 daltons. By contrast, the products of the present invention have weight average molecular weights between about 2,000 and 7,000 daltons and ordinarily at least 90 percent by weight of the polymer chains therein have molecular weights less than 15,000 daltons (all by HPLC using 1.5 molar aqueous sodium chloride as the mobile phase and dextrans as the standard). The products of the invention having weight average molecular weights of about 4,000 or less are preferred for their higher therapeutic indices (the therapeutic index herein is the ratio of the $X_a$ activity to the USP activity, as discussed on a following page). The products of the invention having weight average molecular weights of greater than about 4,000 form a second group of products preferred for their higher specific antithrombotic activities (higher $X_a$ activity).

The analyzable reducing end groups of the polymeric chains of the products of the present invention result from the partial depolymerization process and consist essentially of anhydromannose (i.e. 2,5-anhydromannose), iduronic acid and glucuronic acid moieties (commercial USP heparin itself contains no such end group moieties). Ordinarily from 51–90 percent of these groups are anhydromannose. Although the present invention is in no way conditioned upon or limited by it, the following explanation for the presence of these groups in the products of the invention is suggested.

Heparin is a carbohydrate and it is well known that individual carbohydrate polymer chains contain no more than one end group which can be analyzed, i.e., the so-called reducing end group. Nitrous acid is believed to break heparin chains at glycosidic bonds between N-sulfated glucosamine residues and uronic acid moieties therein (Rosenberg and Rosenberg, ibid., at page 29). In the partial degradation reaction of the present invention only some of these bonds are broken, and such chain breaks ordinarily result in the formation of an analyzable anhydromannose group, although under some conditions the formation of other end groups have been reported (Shively and Conrad, ibid.).

The amounts of each of these types of end groups in polymers of the present invention (which can be conveniently reported in nanomoles per milligram of sample) is determined by the following general procedure (also described by Shively and Conrad, Biochemistry (1976), 15, 3932):

A solution having a known concentration of a heparin sample to be analyzed is prepared. An aliquot of the solution is reduced with tritium-labeled sodium borohydride to introduce a tritium-label selectively into the available reducing end groups in the sample. After destruction of the excess sodium borohydride, the sample is hydrolyzed with 1 normal sulfuric acid and treated with nitrous acid to convert the labeled reducing end group to a mixture of anhydromannitol, beta-1-glucuronosyl anhydromannitol and alpha-1-iduronosyl anhydromannitol, all of which are labeled with tritium, in the anhydromannitol residue. These are separated on paper chromatograms and the amount of tritium in the three components is measured in a scintillation counter using the $^{14}C$-glucose as an internal standard. From the total tritium in these three products, the molar amount of anhydromannose at the reducing ends is calculated. The uronic acid end groups are measured in a separate chromatographic system in which the 1-gulitol (from 1-glucuronic acid) and 1-idonitol (from 1-iduronic acid) are separated.

The following outline more specifically describes the amounts of reagents and the conditions used.

Stock solution: 80 μg. sample dissolved in 1.0 ml. $H_2O$

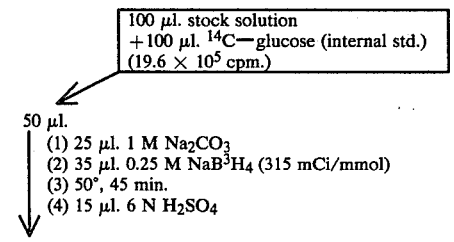

```
100 μl. stock solution
+100 μl. $^{14}C$—glucose (internal std.)
(19.6 × $10^5$ cpm.)
```

50 μl.
 (1) 25 μl. 1 M $Na_2CO_3$
 (2) 35 μl. 0.25 M $NaB^3H_4$ (315 mCi/mmol)
 (3) 50°, 45 min.
 (4) 15 μl. 6 N $H_2SO_4$ -continued 125 μl. reduced sample (5 μl. is analyzed for completeness of reduction)

130 μl.
 (1) dry in stream of air
 (2) dissolve in 120 μl. $H_2O$

120 μl.

90 μl. (aliquot of the 120 μl. amount)
 (1) dry in stream of air
 (2) dissolve in 90 μl. 1 N $H_2SO_4$, 100°, 8 hrs.
 (3) 225 μl. 5.5 M $NaNO_2$, 30 min. rm. temp.
 (4) 90 μl. M $Na_2CO_3$ 405 μl. sample (containing $^3H$-labled end groups
 25 μl. for chromatography)

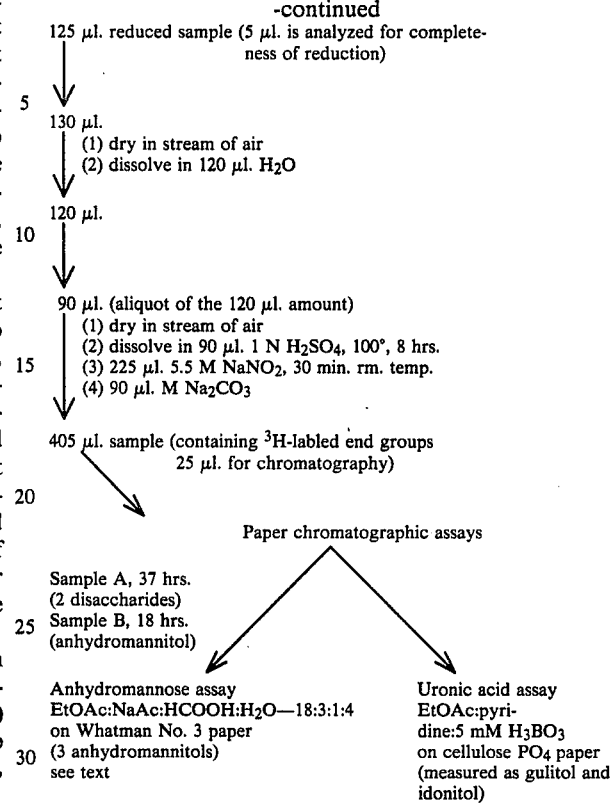

Paper chromatographic assays

Sample A, 37 hrs.
(2 disaccharides)
Sample B, 18 hrs.
(anhydromannitol)

Anhydromannose assay
EtOAc:NaAc:HCOOH:$H_2O$—18:3:1:4
on Whatman No. 3 paper
(3 anhydromannitols)
see text Uronic acid assay
EtOAc:pyridine:5 mM $H_3BO_3$
on cellulose $PO_4$ paper
(measured as gulitol and idonitol)

The weight average molecular weights of the polymers of the invention can also be calculated directly from their total end group analyses (assuming a single analyzable end group per polymer chain). Using this method, the weight average molecular weights of the polymers of Examples 1–5 is calculated to be from about 5,400 to 6,400 daltons. The comparable range of molecular weights measured by the HPLC method (on the same polymers using 1.5 molar sodium chloride as the mobile phase) is 4,600 to 5,700 daltons and ultracentrifugation analyses indicate molecular weights in the range of 4,800 to 6,100 daltons.

Aside from their end groups, the polymers of the present invention contain the same monosaccharide units as do those of the naturally occurring heparin from which they are prepared.

As noted previously, the product of the present invention appears to have an increased therapeutic index, compared to standard heparin. This therapeutic index is the ratio of two well-known in vitro anticoagulant procedures: the $X_a$ ar anti-factor $X_a$ assay (which is described by Yin et al, J. Lab. Clin. Med., Vol. 81, No. 2, February 1973, pages 298–310) and the USP assay, the officially accepted criterion for determining the potency of commercial heparin which is conventionally prescribed for the prevention and treatment of thromboses (described in the United States Pharmacopeia XIX, pages 229–230). Other workers in the field (Barrowcliffe, T. X., Johnson, E. A., Eggleton, C. A., Kemball-Cook, G. and Thomas, D. P., Anticoagulant Activities of High and Low Molecular Weight Heparin Fractions, British Journal o-Haematology, 1979, 41, 573–583) have suggested that the $X_a$ activity of heparin samples correlates with their prophylaxis of venous thrombosis. On the other hand, the USP assay provides a broad measurement of all anticoagulant effects (i.e. including hemorrhagic as well as antithrombotic effects). Thus, althrough no in vitro procedure is available which measures either the antithrombotic or the hemorrhagic property alone, it is believed that the ratio of the $X_a$ and USP activities does provide a meaningful antithrombotic to hemorrhagic therapeutic index.

In order to obtain more dependable and reproducible results, the $X_a$ and USP assays of the products of the invention are run side by side with a commercial USP heparin control. The latter has been rated by the United States Pharmacopeia as to its USP assay (potency) and its $X_a$ and USP assays are conventionally defined as being the same. Thus possible minor day to day variations in the tests are corrected by reference to the rated value of the heparin standard.

The products of this invention ordinarily have $X_a$ activity of at least 100 IU (International Units) per milligram and USP activity of from about 30 to 60 IU per milligram when compared to a standard USP heparin control. The ratio of $X_a$ activity to USP activity of the products of the invention is preferably at least 3:1 and most preferably at least 3.5:1, which compares to the ratio of 1:1 for commercial USP heparin. This ratio is referred to herein as the therapeutic index.

An exception to the foregoing are the products of the invention having weight average molecular weights below about 3,500 (especially 3,300 and below) determined by HPLC using 1.5 molar sodium chloride as the mobile phase, in which the USP activity and the $X_a$ activity both drop. However, the USP activity drops more rapidly with molecular weight than does the $X_a$ activity, with the result that these lower molecular weight products have lower potencies but considerably higher therapeutic indexes.

The process of the invention comprises reacting a heparin salt with from about 5 to 100 milliliters of an aqueous nitrous acid solution per gram of the heparin salt, the aqueous solution containing from about 5 to 80 milligrams of nitrous acid per gram of the heparin salt under controlled conditions of temperature in the range of about 0° to 30° C. and pH in the range of from about 1.5 to 4 until the heparin has partially depolymerized to a product which has
(1) a weight average molecular weight of from about 2,000 to 7,000 daltons, when determined by HPLC using 1.5 molar aqueous sodium chloride as the mobile phase and dextrans as the standard,
(2) polydispersity (D) of less than about 2.5, and
(3) analyzable reducing end groups of which a majority are anhydromannose groups,
terminating the depolymerization reaction and recovering the partially depolymerized product.

The reaction can be carried out and terminated in either of two ways: (a) completely consuming the nitrous acid (i.e. by limiting the amount of nitrous acid in the initial charge so that it is just sufficient to bring the depolymerization reaction to the desired point) or (b) charging a moderate excess of nitrous acid and terminating the reaction (ordinarily by adjusting the pH to 7 or above) when the desired degree of polymerization has been achieved.

The total amount of nitrous acid (nitrite) added per gram of heparin is particularly important in (a) since an excess will degrade the heparin to provide monomers and oligomers with no significant anticoagulant activity. However, the amount required cannot be simply calculated from the stoichiometry of the mixture since only part of the nitrous acid added will actually react with the heparin. The remainder, e.g. perhaps up to 80 percent or more of the amount added, is lost be decomposition or by simply escaping from the reaction mixture. The reaction temperature, the pH and the concentration of the nitrous acid in the aqueous solution are all factors in the efficiency of use of the nitrous acid and must be carefully controlled and balanced (as will be discussed hereinafter). The amount of nitrous acid required for a given set of conditions is easily determined empirically, e.g. by simply varying the amount of nitrous acid in several lots in which the other conditions are kept consistant and measuring the molecular weights of the resulting products.

The reaction can be conveniently monitored by analyzing for the disappearance of nitrite. Alternatively, the peak retention time molecular weight can be monitored as the reaction proceeds and the reaction stopped when approximately the desired molecular weight is reached. It has been found that the peak retention time molecular weights of these polymers are ordinarily less than but within 20 percent of their weight average molecular weights (usually within 10 percent thereof). Thus, the reaction in method (b) is ordinarily terminated when a peak retention time value about 10 percent above the desired weight average molecular weight has been reached (i.e. at approximately 2,500 to 8,000 daltons).

The starting material for the process of the invention can be any available heparin. Commercial USP heparin itself, whether prepared from hog mucosa or from beef lung, is especially suitable. Ordinarily the precursor is utilized in the form of a salt, conveniently an alkali metal or alkaline earth salt. USP heparin is most generally available as the sodium salt, although calcium heparin is also sold in some countries. The particular salt used has not been found to significantly affect the course of the process or the quality of the product of the invention obtained therefrom.

The heparin salt may be added to the aqueous medium either before or after a reagent acid (which establishes the desired pH). The nitrous acid is conveniently formed in situ by adding an aqueous solution of a metal nitrite, e.g. an alkali metal nitrite such as sodium nitrite, to the aqueous acidic solution containing the heparin (the amount of the metal nitrite added being adjusted to provide a 0.01–1 percent by weight aqueous solution of nitrous acid). Normally from about 5 ml. to 100 ml. of the aqueous nitrous acid solution is used per gram of heparin, about 10 ml. of the solution per gram of heparin being particularly preferred.

The temperature of the aqueous reaction system is maintained at a level at which it remains liquid (generally not below about $-5°$ C. and usually at or above 0° C.). On the other hand, the reaction rate is undesirably high and there is danger of product deterioration at temperatures above about 30° C.

The reaction is quite sensitive to changes in pH (e.g. proceeding to completion in as little as 5–10 minutes at pH 1.5 and requiring as much as 10–18 hours at pH 4). Again, balancing the factors of unnecessarily long reaction times with those of loss of control of the reaction and undesirable degradation of the product, it is preferred to operate within the range of pH 1.5 to 4. The pH is maintained in the desired range by means of a reagent acid which should not be so strong or so concentrated that it will react with heparin, but is preferably slightly stronger than nitrous acid. In addition, the reagent acid should be capable of being easily removed from the mixture. Presently preferred are alkanoic acids of 1 to 4 carbon atoms, and most preferred is acetic acid. Other acids, especially mineral acids such as dilute hydrochloric acid or sulfuric acid, may also be used, however.

The concentration of the nitrous acid is preferably kept within the range of the heparin to be depolymerized in the aqueous solution. Lower concentrations are not attractive because of the larger volumes of liquids which must be handled. Higher concentrations can be used but may lead to localized undesirable side reactions.

Ordinarily 0.01 to 0.04 gram of nitrous acid per gram of heparin is required to bring the reaction to the desired point, although this may vary with changing reaction conditions and depending to some degree upon the desired molecular weight of the product. The preferred temperature is from about 15° to 30° C., and the preferred pH range is 2.3 to 3.0. The most preferred pH is approximately 2.8. In a variation of the process, the reaction rate can be increased as much as three fold by lowering the pH from 2.8 to 2.0. This is accomplished by utilizing a greater concentration of the reagent acid in the aqueous solution of heparin (e.g. by increasing the concentration of acetic acid from 1 percent to 40 percent).

In order to terminate the depolymerization reaction completely, the reaction mixture is either frozen and later lyophilized or immediately lyophilized. Lyophilization is continued until the product is isolated as a dry powder. Care is necessary to be certain that all acid is removed, to avoid gradual decomposition of the product. The product can also be isolated by precipitation (after adjusting the pH of the reaction mixture to 8 to 10) with a water-miscible organic solvent of the type employed as described in the art to isolate heparin (for example acetone). Sodium chloride can also be included as a precipitation aid.

The product is obtained as an amorphous white powder. It is soluble in water, since it is obtained as the alkali metal or alkaline earth salt. As noted previously, the yields of product from this process are excellent, ranging up to substantially quantitative.

The following examples are illustrative of the invention, but are in no way limiting thereof. The percentages in the examples are given by weight and the molecular weights are determined by HPLC unless otherwise specifically stated.

EXAMPLE 1

A sample of 20 g. of commercial grade sodium heparin is dissolved in 1 liter of one percent by volume aqueous acetic acid. To this stirred solution is added 160 ml. of 0.4 percent sodium nitrite solution. After stirring at about 20° C. for 3.5 hours the solution is frozen, then lyophilized. A yield of 19.8 grams of a granular white solid is recovered. The following information is obtained on this material:

| Molecular Weight Information (using 1.5 M sodium chloride as the mobile phase) | |
|---|---|
| Peak retention time MW | 6,100 daltons |
| Weight average MW | 4,600 daltons |
| Number average MW | 2,400 daltons |
| Polydispersity | 1.9 |
| Weight percent of the sample having MW above 15,000 daltons | 4.2 |

| -continued | |
|---|---|
| Biological Information | |
| USP potency | 41.0 units/mg |
| $X_a$ potency | 167 |
| Analytical Information | |
| Nuclear magnetic resonance spectral analysis indicates that no N—desulfation has occurred, based on the absence of a peak at 62.5 ppm. | |
| Elemental analysis, found, | 10.4% S |
| | 1.47% N |

EXAMPLE 2

A sample of 10 g. of commercial grade sodium heparin is dissolved in 500 ml. of one percent by volume aqueous acetic acid. To this stirred solution is added 80 ml. of 0.4 percent sodium nitrite solution. After stirring at about 25° C. for 3.5 hours the solution is frozen, then lyophilized. A yield of 8.3 grams of a fluffy white solid is recovered. The following information is obtained on this material:

| Molecular Weight Information (using 1.5 M sodium chloride as the mobile phase | |
|---|---|
| Weight average MW | 5,400 daltons |
| Number average MW | 2,400 daltons |
| Polydispersity | 2.3 |
| Weight percent of the sample having MW above 15,000 daltons | 7.2 |
| Biological Information | |
| USP potency | 37 units/mg |
| $X_a$ potency | 210 units/mg |
| Analytical Information | |
| Nuclear magnetic resonance spectral analysis indicates that no N—desulfation has occurred since no peak occurs at 62.5 ppm. | |
| Elemental analysis, found: | 1.73% N |

EXAMPLE 3

Using the procedure of Example 2, a 20 g. sample of sodium heparin is partially depolymerized. The following information is obtained on the resulting product:

| Molecular Weight Information (using 1.5 M sodium chloride as the mobile phase) | |
|---|---|
| Weight average MW | 5,700 daltons |
| Number average MW | 2,800 daltons |
| Polydispersity | 2.2 |
| Weight percent of the sample having MW above 15,000 daltons | 6.9 |
| Biological Information | |
| USP potency | 33 units/mg |
| $X_a$ potency | 200 units/mg |
| Analytical Information | |
| Nuclear magnetic resonance spectral analysis indicates that no N—desulfation has occurred, since no peak occurs at 62.5 ppm. | |
| Elemental analysis, found | 1.73% N |

EXAMPLE 4

Using the procedure of Example 2, a 20 g. sample of sodium heparin is partially depolymerized to provide 18.5 grams of a fluffy white solid product. The following information is obtained on this material:

| Molecular Weight Information (using 1.5 M sodium chloride as the mobile phase) | |
| --- | --- |
| Weight average MW | 5,500 daltons |
| Number average MW | 2,700 daltons |
| Polydispersity | 2.2 |
| Weight percent of the sample having MW above 15,000 daltons | 8.6 |
| Biological Information | |
| USP potency | 40 units/mg |
| $X_a$ potency | 200 units/mg |
| Analytical Information | |
| Nuclear magnetic resonance spectral analysis indicates that no N—desulfation has occurred. | |
| Elemental analysis, found: | 1.79% N |
| Residue on ignition | 38.9% |

EXAMPLE 5

Using the procedure of Example 2, a 50 g. sample of sodium heparin is partially depolymerized to provide 46.6 grams of a fluffy white solid product. The following information is obtained on this material:

| Molecular Weight Information (using 1.5 M sodium chloride as the mobile phase) | |
| --- | --- |
| Weight average MW | 5,100 daltons |
| Number average MW | 2,200 daltons |
| Polydispersity | 2.3 |
| Weight percent of the sample having MW above 15,000 daltons | 3.5 |
| Biological Information | |
| USP potency | 33 units/mg |
| $X_a$ potency | 167 units/mg |

EXAMPLE 6

The products of Example 1 through 5 are analyzed for the reducing end groups present. The results are shown in Table I:

TABLE I

| | End Group Analyses (Nanomoles/mg sample) | | |
| --- | --- | --- | --- |
| Product of Ex. | Anhydro-mannose | Iduronic acid | Glucuronic acid |
| 1 | 98.0 | 39.6 | 19.5 |
| 2 | 109.5 | 42.2 | 31.9 |
| 3 | 105.0 | 36.3 | 14.8 |
| 4 | 113.4 | 30.6 | 10.9 |
| 5 | 112.7 | 30.8 | 13.0 |
| parent heparin | not detectable | not detectable | not detectable |

The weight average molecular weights of the products of Examples 1–5 range from 5,400 to 6,400 when calculated from the total of the end group analyses.

EXAMPLE 7

The use of the process of the invention in which the endpoint of the depolymerization reaction is determined by the disappearance of the nitrous acid.

A sample of 5 g. of commercial grade sodium heparin is dissolved in 250 ml. of 40 percent by volume aqueous acetic acid. To this stirred solution is added 20 ml. of 0.4 percent aqueous sodium nitrite solution. The pH of the solution is 1.8. The solution is stirred at about 20° C. for about 18 hours, then lyophilized. The USP potency of the resulting solid is 43 units/mg., its weight average molecular weight is 6,600 daltons in 0.5 M sodium sulfate solution and 5,500 daltons (estimated) in 1.5 M sodium chloride.

The foregoing procedure is followed in two additional runs except that the volume of the 0.4 percent aqueous sodium nitrite solution is varied. The results are shown in Table II, the foregoing run (Lot A) being included for comparison.

TABLE II

| Lot No. | NaNO2 Solution (ml.) | USP Potency (Units/mg) | Wt. Av. MW (0.5 M) Na2SO4 | Wt. Av. MW-estd. (1.5 M NaCl) |
| --- | --- | --- | --- | --- |
| A | 20 | 43 | 6,600 | 5,500 |
| B | 30 | 33 | 5,500 | 4,300 |
| C | 40 | 27 | 4,500 | 3,000 |

Each of the foregoing products falls within the invention, i.e. has a polydispersity of less than 2.5 and analyzable reducing end groups of which a majority are anhydromannose groups.

EXAMPLE 8

The use of the process of the invention in which the final endpoint of the depolymerization is determined by the disappearance of the nitrous acid, but demonstrating that the process can be stopped at intermediate points, if desired, to obtain product of higher molecular weight.

A sample of 5 g. of commercial grade sodium heparin is dissolved in 250 ml. of 5 percent by volume aqueous acetic acid. To this stirred solution is added 40 ml. of 0.4 percent sodium nitrite solution. The pH of this solution is 2.5. The solution is stirred at about 20° C. Samples of 25 ml. are removed periodically as shown in Table III below, frozen, then lyophilized. The USP potencies and weight average molecular weights in 0.5 M sodium sulfate solution and the estimated weight average molecular weights in 1.5 M sodium chloride of these lots are as follows:

TABLE III

| Lot No. | Reaction Time | Wt. of Solid (g) | USP Potency (Units/mg) | Wt. Av. MW (0.5 M Na2SO4) | Wt. Av. MW-estd. (1.5 M NaCl) |
| --- | --- | --- | --- | --- | --- |
| A | 35 min. | 0.52 | 59 | 7,200 | 6,300 |
| B | 1 hr. | 0.52 | 40.6 | 6,000 | 5,000 |
| C | 3 hrs. | 0.50 | 28 | 4,800 | 3,200 |
| D | 18 hrs. | 3.50 | 26 | 4,600 | 3,000 |

In a similar run, a sample of 5 g. of commercial grade heparin is dissolved in 250 ml. of one percent by volume aqueous acetic acid. To this stirred solution is added 40 ml. of 0.4 percent aqueous sodium nitrite solution. The pH of this solution is 2.8. The solution is stirred at about 20° C. Samples of 50 ml. are removed periodically as in the foregoing run, frozen, then lyophilized. The final sample is the balance of the reaction mixture. The results obtained (as in the foregoing run) from these lots are shown in Table IV.

TABLE IV

| Lot No. | Reaction Time | Wt. of Solid (g) | USP Potency (Units/mg) | Wt. Av. MW (0.5 M Na2SO4) | Wt. Av. MW-estd. (1.5 M NaCl) |
| --- | --- | --- | --- | --- | --- |
| E | 15 min. | 0.88 | 124 | 21,900 | 17,000 |
| F | 30 min. | 0.85 | 116 | 19,700 | 15,000 |
| G | 60 min. | 0.88 | 104 | 13,000 | 10,000 |
| H | 180 min. | 0.90 | 65 | 6,600 | 5,500 |

TABLE IV-continued

| Lot No. | Reaction Time | Wt. of Solid (g) | USP Potency (Units/mg) | Wt. Av. MW (0.5 M Na₂SO₄) | Wt. Av. MW-estd. (1.5 M NaCl) |
|---|---|---|---|---|---|
| I | 18 hr. | 2.01 | 30 | 4,500 | 3,000 |

Thus it is clear that the reaction can be followed and stopped at the desired point. The products of lots A–D and H–I fall within the invention, i.e. having polydispersity of less than 2.5 and analyzable reducing end groups of which a majority are anhydromannose groups.

EXAMPLE 9

The use of the process of the invention in which the depolymerization reaction is terminated when the desired degree of depolymerization has been achieved.

Ten grams of USP heparin are dissolved in 100 ml. of water and cooled to 5° C., and a solution of 160 milligrams of sodium nitrite in 1.6 milliliters of water is added. The pH is adjusted to 2.8, and the reaction mixture is stirred without additional cooling for 1½ hours. The temperature at the end of the reaction is 18° C. The reaction is terminated by adjusting the pH to 8 using 4 N sodium hydroxide. The partially depolymerized heparin is isolated by adding 1.2 g. of sodium chloride followed by 250 milliliters of acetone. A syrupy oil separates out at 0° C. It is recovered by decanting the clear upper layer. On trituration with methanol, 10.1 grams of solid white heparin are recovered, having a USP potency of 41 units per milligram and a peak retention time molecular weight of 6,000 daltons (using 1.5 M sodium chloride as the mobile phase).

The foregoing procedure is used in two additional runs except that the amount of sodium nitrite in the charge is varied. The results are shown in Table V, the foregoing run (Lot A) being included for comparison.

TABLE V

| Lot No. | NaNO₂ (mg) | Yield (grams) | Molecular Weight[1] | $X_a$ Potency | USP Potency | Therapeutic Index $X_a$/USP |
|---|---|---|---|---|---|---|
| A | 160 | 10.1 | 6,000 | 147 | 41 | 3.6 |
| B | 220 | 10.1 | 3,000 | 112 | 8(5) | 14 |
| C | 640 | 7.0 | 2,100 | 68 | <3 | >23 |

[1]Peak retention time molecular weights determined using 1.5 M sodium chloride as the mobile phase. The comparable weight average molecular weights are about 6,500, 3,300 and 2,300 respectively.

These products (Lots A, B and C in Table V) all have polydispersities less than 2.5 and analyzable reducing end groups of which a majority are anhydromannose.

EXAMPLE 10

Carrying the depolymerization of a sample of USP heparin to completion following the procedure of the present invention utilizing an excess of nitrous acid.

One gram of USP heparin is dissolved in 10 ml. of water and cooled to −5° C. and a solution of about 2.3 grams of barium nitrite (10 mmoles) and 0.98 gram of sulfuric acid (10 mmole) in 40 ml. of water is added (the latter solution also being at −5° C.). The reaction mixture is stirred without additional cooling for about 1 hour. The reaction is terminated by neutralizing with sodium carbonate and the depolymerized heparin product is isolated by lyophilization. The product is 1.7 grams of a pale yellow powder having a weight average molecular weight of 1,000 and a number average molecular weight of 900 (using 1.5 M sodium chloride as the mobile phase).

It is found to have no $X_a$ potency and no USP potency.

What is claimed is:

1. A process which comprises reacting a heparin salt with from about 5 to 100 milliliters of an aqueous nitrous acid solution per gram of the heparin salt, the aqueous solution containing from about 5 to 80 milligrams of nitrous acid per gram of the heparin salt under controlled conditions of temperature in the range of about 0° C. to 30° C. and pH in the range of from about 1.5 to 4 until the heparin has partially depolymerized to a product which has
    (1) a weight average molecular weight of from about 2,000 to 7,000 daltons, when determined by HPLC using 1.5 molar aqueous sodium chloride as the mobile phase and dextrans as the standard,
    (2) a polydispersity (D) of less than about 2.5, and
    (3) analyzable reducing end groups of which the majority are anhydromannose groups,
terminating the depolymerization reaction and recovering the partially depolymerized product.

2. A process according to claim 1 wherein the proportion of nitrous acid charged is just sufficient to bring the depolymerization reaction to the desired point and the reaction is terminated upon disappearance of the nitrous acid from the reaction mixture.

3. A process according to claim 1 wherein the proportion of nitrous acid charged is in excess of the quantity required to bring the depolymerization reaction to the desired point and the reaction is terminated when the desired degree of depolymerization has been achieved.

4. A process according to claim 1 wherein the depolymerization is carried out in the presence of a lower alkanoic acid.

5. A process according to claim 2 wherein the depolymerization is carried out in the presence of from about 0.5 to 10 percent by volume of acetic acid.

6. A process according to claim 1 wherein the depolymerization is carried out in an aqueous system in which the pH is adjusted by means of a mineral acid.

7. A depolymerization process according to claim 3 wherein the depolymerization reaction is terminated when the peak retention time molecular weight of the heparin reaches a desired value in the range of 2,500 to 8,000 daltons, when determined by HPLC, using 1.5 molar aqueous sodium chloride as the mobile phase and dextrans as the standard.

* * * * *